US006355848B1

(12) United States Patent
Antons et al.

(10) Patent No.: US 6,355,848 B1
(45) Date of Patent: Mar. 12, 2002

(54) METHOD FOR PRODUCING OPTICALLY ACTIVE ALCOHOLS

(75) Inventors: Stefan Antons, Leverkusen (DE); Andreas Schulze Tilling, League City, TX (US); Erich Wolters, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/600,965

(22) PCT Filed: Jan. 16, 1999

(86) PCT No.: PCT/EP99/00234

§ 371 Date: Jul. 25, 2000

§ 102(e) Date: Jul. 25, 2000

(87) PCT Pub. No.: WO99/38824

PCT Pub. Date: Aug. 5, 1999

(30) Foreign Application Priority Data

Jan. 31, 1998 (DE) .......................................... 198 03 893

(51) Int. Cl.⁷ .......................... C07C 27/00; C07C 29/14
(52) U.S. Cl. ........................................ 568/881; 568/864
(58) Field of Search ................................... 568/864, 881

(56) References Cited

U.S. PATENT DOCUMENTS 5,149,680 A * 9/1992 Kitson et al. ................ 502/185
5,731,479 A * 3/1998 Antons ........................ 568/864

OTHER PUBLICATIONS

Chemistry Letters, (month unavailable) 1984, pp. 1389–1392, Saito et al, Combination of Borne–Dimethyl Sulfide Complex with Catalytic Sodium Tetrahydroborate as a Selective Reducing Agent for α–Hydroxy Esters, Versatile Chiral Building Block from (S)–(–)–Malic Acid.

* cited by examiner

*Primary Examiner*—Samuel Barts
*Assistant Examiner*—Elvis O. Price
(74) *Attorney, Agent, or Firm*—Joseph C. Gil; Richard E. L. Henderson

(57) ABSTRACT

The invention relates to a process for the preparation of optically active alcohols from optically active carboxylic acids by reducing an optically active carboxylic acid with hydrogen in the presence of a catalyst comprising ruthenium and at least one further metal or transition metal having an atomic number in the range of from 23 to 82.

10 Claims, No Drawings

METHOD FOR PRODUCING OPTICALLY ACTIVE ALCOHOLS

This is the National Phase Application of PCT/EP99/00234, filed Jan. 16, 1999.

The present invention relates to a process for the preparation of optically active alcohols by catalytic reduction of the corresponding optically active carboxylic acids with hydrogen.

It is already known that optically active alcohols can be prepared by catalytic hydrogenation of the corresponding carboxylic acids on ruthenium catalysts (see EP-A 717 023). The suitable reaction conditions stated therein are temperatures in the range from 50 to 150° C. and pressures in the range from 5 to 250 bar.

In the preparation of S-1,2-propanediol (according to an older nomenclature also to be referred to as L-1,2-propanediol), this gave enantiomeric excesses of more than 97% at a yield of at most 88% and a reaction temperature of 80° C. In the corresponding hydrogenation of S-malic acid (according to an older nomenclature also to be referred to as L-malic acid), this gave S-1,2,4-butanetriol in a purity of 97% at 80° C. A value for the enantiomeric excess was not given.

The enantiomeric excesses of the alcohols prepared in this manner do not yet entirely meet the high requirements for intermediates of active compounds. Moreover, the chemical yields that can be obtained and the reaction times required are not yet entirely satisfactory.

There is therefore still a need for a process for preparing optically active alcohols from the corresponding carboxylic acids in which the overall combination of the enantiomeric excess that can be obtained, the chemical yield that can be obtained and the reaction time required is more favourable than before.

A process for the preparation of optically active alcohols from optically active carboxylic acids has now been found which is characterized in that optically active carboxylic acids are reduced with hydrogen in the presence of a catalyst which, in addition to ruthenium, comprises at least one further metal or transition metal having atomic numbers in the range from 23 to 42.

Examples of optically active carboxylic acids which can be used in the process according to the invention are those of the formula (I):

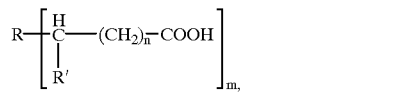

in which
m is 1, 2 or 3,
n is zero or an integer from 1 to 5 and
R' is a monovalent radical selected from the group comprising linear and branched $C_1$–$C_{12}$-alkyl, $C_7$–$C_{12}$-aralkyl, $C_6$–$C_{10}$-aryl and $C_1$–$C_{12}$-alkoxy radicals or is hydroxyl or halogen, and
if m=1
R is a monovalent radical selected from the group comprising linear and branched $C_1$–$C_{12}$-alkyl, $C_7$–$C_{12}$-aralkyl, $C_6$–$C_{10}$-aryl and $C_1$–$C_{12}$-alkoxy radicals or is a halogen or hydroxyl radical which is different from R',
if m=2
R is absent or is a divalent radical selected from the group comprising linear and branched $C_1$–$C_{12}$-alkyl and $C_7$–$C_{12}$-aralkyl radicals, and
if m=3
R is a trivalent radical selected from the group comprising linear and branched $C_1$–$C_{12}$-alkyl and $C_7$–$C_{12}$-aralkyl radicals,
giving optically active alcohols of the formula (II):

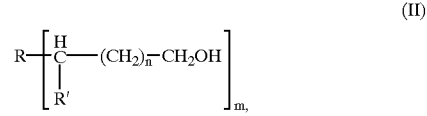

in which
m, n, R' and R are as defined for the formula (I).
Preferably, in the formulae (I) and (II),
m is 1 or 2,
n is zero, 1 or 2 and
R' is linear or branched $C_1$–$C_4$-alkyl, benzyl, hydroxyl, fluorine, chlorine or bromine, and
R is different from R' and is linear or branched $C_1$–$C_4$-alkyl, benzyl, hydroxyl, fluorine or chlorine.
A further preference is for one of the radicals R' and R to be hydroxyl.

If m is 2 or 3, i.e. there are 2 or 3 molecular moieties CH(R')—(CH$_2$)$_n$—COOH present in the starting material, these molecules can be identical or different in respect of the definitions of n and R'.

If R' and R are alkyl, aralkyl, aryl and/or alkoxy radicals, these can optionally be substituted, e.g. by halogen, hydroxyl, $C_1$–$C_4$-alkoxy, thiol, amino and/or $C_1$–$C_4$-alkylamino radicals. R' and/or R preferably contain fewer than four such substituents. Reductions and/or cleavage reactions may also take place at such substituents.

If R' and R are alkyl, aralkyl, aryl or alkoxy radicals, these can optionally contain heteroatoms, e.g. oxygen, sulphur and/or nitrogen atoms, in the alkyl chain and/or in the aryl moiety. Preferably, fewer than 3 such heteroatoms are present.

If R' and R are aralkyl or aryl radicals, these can also be partially or fully hydrogenated.

If a plurality of COOH groups is present in a compound of the formula (I), it is possible, after the reduction of one of these COOH groups to the CH$_2$OH groups, for lactone formation with one of the remaining COOH groups to occur.

Particularly preferably, the acid used in the process according to the invention is optically active lactic acid, optically active tartaric acid, optically active 2-chloropropionic acid, optically active 4-chloro-3-hydroxybutyric acid or optically active malic acid, giving optically active propane-1,2-diol, optically active 1,2,3,4-butanetetraol, optically active 2-chloropropanol, optically active 4-chloro-1,3-butanediol or optically active 1,2,4-butanetriol respectively.

Suitable catalysts for the process according to the invention are, for example, bimetallic ruthenium/metal X catalysts and trimetallic ruthenium/metal X/metal Y catalysts, all of which can be used as such or when applied to a support, where X and Y in each case represent a metal having an atomic number in the range from 23 to 82. The catalysts can comprise ruthenium and the metals X and, if appropriate, the metals Y in different forms, for example in elemental form, in colloidal form, in the form of compounds of ruthenium and the metals X or of ruthenium and the metals X and Y or in the form of an intermetallic compound of ruthenium and the metal X and, if appropriate, the metal Y. If the catalysts are employed unsupported, they can be present, for example, in colloidal form or as a finely dispersed solid. Examples of catalysts are finely dispersed ruthenium/rhenium, ruthenium/osmium, ruthenium/iron, ruthenium/cobalt, ruthenium/rhodium, ruthenium/palladium, ruthenium/platinum, ruthenium/copper, ruthenium/zinc, ruthenium/silver, ruthenium/tin, ruthenium/germanium, ruthenium/gallium, ruthenium/lead, ruthenium/rhenium/copper, ruthenium/rhenium/silver and ruthenium/rhenium/tin particles, for example in metallic form or in the form of their oxides, hydroxides, halides, nitrates, carboxylates or acetylacetonates.

Suitable supports are, for example, carbons, carbon blacks, graphites, aluminium oxides, silicon dioxides, silicates, zeolites and aluminas. Supported catalysts can comprise, for example, from 1 to 50% by weight of metal, in elemental form or in the form of compounds.

The catalysts to be employed can, if appropriate, be modified by a treatment with sulphur compounds, for example with thioether.

Preference is given to catalysts comprising unsupported rhenium and ruthenium and having a high specific surface, for example of from 50 to 150 $m^2/g$. Such catalysts can be prepared, for example, by reductively depositing, by action of hydrogen, rhenium from a rhenium solution on a ruthenium oxide hydrate with a high surface (for example from 50 to 300 $m^2/g$). What is obtained is a bimetallic catalyst having a high surface, where the two metals are in intimate contact. In principle, a second metal can be deposited during the preparation of the catalyst or in situ during the hydrogenation reaction.

Based on 1 mol of optically active carboxylic acid employed, it is possible to use as catalyst e.g. 0.1 to 30 g of metal or metal compounds or 1 to 100 g of supported catalysts containing metal or metal compounds.

The process according to the invention is in general cared out in the presence of a solvent for the optically active carboxylic acids and the optically active alcohols. Examples of suitable solvents are water, water-miscible organic solvents and mixtures of the two. Water-miscible solvents which may be mentioned are lower alcohols and water-miscible ethers. Preferred solvents are water and mixtures containing water and lower alcohols or tetrahydrofuran.

The process according to the invention can be carried out, for example, at temperatures in the range from 0 to 150° C. and pressures in the range from 5 to 300 bar. Preference is given to temperatures from 40 to 130° C. and pressures from 50 to 250 bar. Particular preference is given to temperatures from 30 to 80° C. and pressures from 150 to 250 bar.

To work up the reaction mixture, it is possible for example firstly to cool it and separate off the catalyst, e.g. by filtration, and then to neutralize the product solution, for example with aqueous sodium hydroxide solution, to remove the highly volatile components present (in general solvent and water of reaction) by distillation, if appropriate under reduced pressure, and fractionate the residue under vacuum. The catalyst which has been separated off can be re-used, as can the solvent. The process according to the invention can be carried out continuously, semi-continuously or batchwise. Suitable reactors are, for example, stirred tanks and trickle-bed reactors. The process is advantageously carried out as a batch feed process, where the catalyst is initially charged in the solvent and the acid is pumped in in the amounts consumed during the hydrogenation. Owing to this, it is possible to keep the acid concentration in the reactor at a low level, which has a positive effect on the operating life of the catalyst and on the yield and reduces the corrosiveness of the reaction medium.

When optically active malic acid is reduced by the process according to the invention, the reaction mixture obtained can be converted directly, i.e. without prior separation of byproducts, into the optically active 3-hydroxytetrahydrofuran, for example by firstly cooling it, separating off the catalyst, removing the highly volatile components by distillation, if appropriate under slightly reduced pressure, adding p-toluenesulphonic acid and carrying out fractional distillation under reduced pressure.

In the reduction according to the invention of optically active malic acid, in addition to optically active 1,2,4-butanetriol, optically active 3,4-dihydroxybutyric acid is generally obtained, some of which lactonizes even under the reaction conditions to give the optically active 3-hydroxybutyrolactone. This is in particular the case if the reaction is terminated at from 50 to 60% of the hydrogen consumption which would be required for the complete reduction to 1,2,4-butanetriol, the highly volatile components are removed, the residue is neutralized, for example with aqueous sodium hydroxide solution, and the 1,2,4-butanetriol is separated off, for example by distillation. After the 3,4-dihydroxybutyric acid has been liberated and lactonized to the optically active 3-hydroxybutyrolactone by addition of acid, for example trifluoroacetic acid (see Chem. Lett. (1984), 1389), the optically active 3-hydroxybutyrolactone can be separated off by distillation.

Surprisingly, catalysts to be used according to the invention, in particular those comprising ruthenium and rhenium, have a considerably higher performance in the hydrogenation of optically active carboxylic acids than a monometallic ruthenium catalyst. Using the process according to the invention, it is possible, in a simple manner, to produce, even on an industrial scale, optically active alcohols having a higher purity, a higher enantiomeric excess, in a higher yield, at lower temperatures and/or with shorter reaction times than when the known hydrogenation processes are used. In particular, the overall combination of the enantiomeric excess that can be obtained, the chemical yield that can be obtained and the reaction time required is more favourable than in the prior art.

EXAMPLES

Example 1 a) Catalyst Preparation

In a 0.71 stainless steel autoclave, 62.9 g of water-moist $RuO_2$ (comprising 7.61% by weight of Ru) and 6.3 g of $Re_2O_7$ (comprising 76.9% by weight of Re) were initially charged in 100 ml of water. The autoclave was flushed 2 times each with nitrogen and then with hydrogen, a hydrogen pressure of 100 bar was applied and the autoclave was heated with stirring (800 rpm) to 120° C. After this temperature had been reached, the hydrogen pressure was increased to 150 bar and these conditions were maintained for 1 hour. This gave a Ru/Re catalyst with a specific surface of 70 $m^2g$ (determined by the BET method).

b) Hydrogenation of S-malic Acid

The autoclave was cooled to 60° C. and vented, and 278 g of an 18.9% by weight strength aqueous S-malic acid solution were added. The mixture was subsequently stirred at 60° C. and a hydrogen pressure of 200 bar until the hydrogen uptake had ended (24 hours). After cooling to room temperature, the catalyst was filtered off, the remaining reaction mixture was neutralized with aqueous sodium hydroxide solution and the water was distilled off from the crude solution obtained. 42.0 g of a colourless viscous liquid remained, which was distilled at a pressure of 1 mbar. After a forerunning consisting of butanediols, 33.9 g of 97.9% by weight strength S-1,2,4-butanetriol were obtained (b.p. 133° C./1 mbar, ee=98.8%). This corresponds to a yield of 79.8% of theory, based on the S-malic acid employed.

Example 2

Course of the Reaction

Example 1 was repeated, and the course of the reaction was monitored by taking samples. The change in the composition of the reaction mixture over time is shown in Table 1. It can be seen, in particular, after which reaction time relatively great amounts of S-3,4-dihydroxybutyric acid and S-3-hydroxybutyrolactone are present in the reaction mixture.

TABLE 1

| Components in the reaction mixture [GC %] | Reaction time [h] | | | | |
|---|---|---|---|---|---|
| | 4 | 10 | 16 | 20 | 24 |
| S-malic acid | 58 | 15 | 1 | <1 | <1 |
| S-1,2,4-Butanetriol | 7.5 | 24.5 | 48.5 | 64.5 | 78 |
| S-3,4-Dihydroxybutyric acid | 22 | 37.5 | 30 | 18 | 3.5 |
| S-3-Hydroxybutyrolactone | 7 | 15 | 14 | 11.5 | 9 |

Example 3 a) Catalyst Preparation

In a 3l stainless steel autoclave, 234.6 g of water-moist $RuO_2$ (comprising 8.2% by weight of Ru) and 25.2 g of $Re_2O_7$ (comprising 76.9% by weight of Re) were initially charged in 400 ml of water. The autoclave was flushed 2 times each with nitrogen and then with hydrogen, a hydrogen pressure of 100 bar was applied and the autoclave was heated with stirring (800 rpm) to 120° C. After this temperature had been reached, the hydrogen pressure was increased to 150 bar and these conditions were maintained for 1 hour.

b) Hydrogenation of S-malic Acid By the Batch Feed Process

The autoclave was cooled to 70° C. and the hydrogen pressure was increased to 200 bar. Over the course of 9.5 hours, 1112 g of an 18.9% by weight strength aqueous S-malic acid solution were then added, and the mixture was stirred until the uptake of hydrogen had ended (5 hours). After cooling to room temperature, the liquid components of the autoclave content were removed via a riser tube with frit. For further hydrogenations, the catalyst remained in the autoclave (see Examples 4 to 6). From the crude solution obtained, the water was distilled off. 154.1 g of a colourless viscous liquid remained, which was distilled at a pressure of 1 mbar. After a forerunning consisting of butanediols, 135.8 g of 98.9% by weight strength S-1,2,4-butanetriol were obtained (b.p. 133° C./1 mbar, ee=98.1%/o). This corresponds to a yield of 80.7% of theory, based on the S-malic acid employed.

Examples 4 to 6

Repeated Use of Catalyst

Example 3 b) was repeated 3 times, in each case using the recovered catalyst. For details see Table 2.

TABLE 2

| | Number of times recycled | Yield *) | ee value |
|---|---|---|---|
| Example 4 | 1 | 78.2% | 99.1% |
| Example 5 | 2 | 81.4% | 98.9% |
| Example 6 | 3 | 77,5% | 99,1% |

*) % of theory, based on the S-malic acid employed

Examples 7 to 10

Comparative Examples

Example 3 was repeated, but without using $Re_2O_7$ when preparing the catalyst. Different temperatures were used. For details see Table 3.

TABLE 3

| | Temperature | Reaction time [hours] | Yield [in % of theory] | ee value |
|---|---|---|---|---|
| Example 7 | 60° C. | 24 | no conversion | |
| Example 8 | 80° C. | 24 | 19.9% | 9.9% |
| Example 9 | 100° C. | 19 | 68.2% | 78.4% |
| Example 10 | 120° C. | 25 | 45.3% | 0.1% |

Examples 11 and 12

Example 1 was repeated, but using, instead of $Re_2O_7$, on the one hand a corresponding amount of an acidic tin(II) chloride solution and on the other hand a corresponding amount of iron(II) oxalate. The results are shown in Table 4.

TABLE 4

| | Catalyst | Reaction time [hours] | Yield [in % of theory] | ee value |
|---|---|---|---|---|
| Example 11 | Ru/Sn | 30 | 88.4 | 93.4% |
| Example 12 | Ru/Fe | 24 | 62.9 | 94.3% |

What is claimed is:

1. A process for the preparation of optically active alcohols from optically active carboxylic acids comprising reducing an optically active carboxylic acid with hydrogen in the presence of a catalyst comprising ruthenium and at least one further metal or transition metal having an atomic number in the range of from 23 to 82, whereby the optically active alcohols are obtained in higher enantiomeric excess than when using a catalyst containing ruthenium but not the further metal or transition metal.

2. A process according to claim 1 wherein
   (i) the optically active carboxylic acid has formula (I)

(I)

wherein
   m is 1, 2, or 3,
   n is zero or an integer from 1 to 5 and
   R' is a monovalent radical selected from the group consisting of linear and branched $C_1$–$C_{12}$-alkyl, $C_7$–$C_{12}$-aralkyl, $C_6$–$C_{10}$-aryl, $C_1$–$C_{12}$-alkoxy radicals or is hydroxyl or halogen, and if m is 1, then R is different from R' and is a monovalent radical selected from the group consisting of linear and branched $C_1$–$C_{12}$-alkyl, $C_7$–$C_{12}$-aralkyl, $C_6$–$C_{10}$-aryl, $C_1$–$C_{12}$-alkoxy radicals or is a halogen or hydroxyl radical, if m is 2, then R is absent or is a divalent radical selected from the group consisting of linear and branched $C_1$–$C_{12}$-alkyl and $C_7$–$C_{12}$-aralkyl radicals, and if m is 3, then R is a trivalent radical selected from the group consisting of linear and branched $C_1$–$C_{12}$-alkyl and $C_7$–$C_{12}$-aralkyl radicals, and if m is 3, then R is a trivalent radical selected from the group consisting of linear and branched $C_1$–$C_{12}$-alkyl and $C_7$–$C_{12}$-aralkyl radicals, and the resultant optically active alcohol has the formula (II)

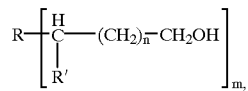

(II)

wherein m, n, R' and R are as defined for formula (I).

3. A process according to claim 1 wherein the optically active carboxylic acid is optically active lactic acid, optically active tartaric acid, optically active 2-chloropropionic acid, optically active 4-chloro-3-hydroxybutyric acid, or optically active malic acid.

4. A process according to claim 1 wherein the catalyst is a bimetallic ruthenium/metal X catalyst or a trimetallic ruthenium/metal X/metal Y catalyst, wherein X and Y independently represent a metal having an atomic number in the range of from 23 to 82.

5. A process according to claim 4 wherein ruthenium and the metal X and the optional metal Y are present in elemental form, in colloidal form, in the form of compounds of ruthenium and the metal X and the optional metal Y, or in the form of an intermetallic compound of ruthenium and the metal X and the optional metal Y.

6. A process according to claim 1 wherein the catalyst comprises unsupported rhenium and ruthenium and has a specific surface of from 50 to 150 $m^2/g$.

7. A process according to claim 1 wherein 0.1 to 30 g of the metal or metal compound or 1 to 100 g of a supported catalyst comprising the metal or metal compound is used per 1 mol of optically active carboxylic acid.

8. A process according to claim 1 wherein the temperatures are in the range of from 0 to 150° C. and the pressures are in the range of from 5 to 300 bar.

9. A process according to claim 1 wherein the resultant reaction mixture obtained after the reduction is completed is worked up by cooling the mixture, separating off the catalyst from the mixture, neutralizing the solution from which the catalyst is separated, distilling off the highly volatile components present in the solution, and fractionating the distillation residue under reduced pressure.

10. A process for the preparation and separation of optically active 1,2,4-butanetriol, optically active 3,4-dihydroxybutyric acid, and, optionally, optically active 3-hydroxybutyrolactone comprising (a) partially reducing optically active malic acid by the process of claim 1, (b) terminating the reduction at from 50 to 60% of the hydrogen consumption required for complete reduction to 1,2,4-butanetriol, (c) separating off the highly volatile components, (d) neutralizing the resultant residue and separating off 1,2,4-butanetriol, (e) liberating the residual optically active 3,4-dihydroxybutyric acid, and (f) optionally, lactonizing the optically active 3,4-dihydroxybutyric acid by addition of acid and distilling off the resultant optically active 3-hydroxybutyrolactone.

* * * * *